(12) United States Patent
Sim

(10) Patent No.: US 11,094,403 B2
(45) Date of Patent: Aug. 17, 2021

(54) METHOD AND APPARATUS FOR COLLECTING TEST DATA FROM USE OF A DISPOSABLE TEST KIT

(71) Applicant: CELL ID PTE LTD, Singapore (SG)

(72) Inventor: Lye Hock Sim, Singapore (SG)

(73) Assignee: CELL ID PTE LTD, Singapore (SG)

( * ) Notice: Subject to any disclaimer, the term of this patent is extended or adjusted under 35 U.S.C. 154(b) by 675 days.

(21) Appl. No.: 15/741,233

(22) PCT Filed: Jun. 29, 2015

(86) PCT No.: PCT/SG2015/050185
§ 371 (c)(1),
(2) Date: Dec. 29, 2017

(87) PCT Pub. No.: WO2017/003368
PCT Pub. Date: Jan. 5, 2017

(65) Prior Publication Data
US 2018/0197623 A1 Jul. 12, 2018

(51) Int. Cl.
*G16H 10/60* (2018.01)
*B01L 3/00* (2006.01)
(Continued)

(52) U.S. Cl.
CPC .............. *G16H 10/60* (2018.01); *B01L 3/545* (2013.01); *G06F 3/0482* (2013.01);
(Continued)

(58) Field of Classification Search
None
See application file for complete search history.

(56) References Cited

U.S. PATENT DOCUMENTS

| | | | |
|---|---|---|---|
| 6,702,988 B1 * | 3/2004 | Sagona | B01L 3/508 422/404 |
| 2002/0021828 A1 * | 2/2002 | Papier | G06F 19/326 382/128 |

(Continued)

FOREIGN PATENT DOCUMENTS

| | | |
|---|---|---|
| CN | 102687022 A | 9/2012 |
| JP | 2013170835 A | 9/2013 |

(Continued)

OTHER PUBLICATIONS

Surabattula, Deepti et al., Usability of Home Cholesterol Test Kits and How Their Results Impact Patients' Decisions, Int'l J. of Industrial Ergonomics 39, 2009, pp. 167-173, https://www.sciencedirect.com/science/article/pii/S0169814108001224 (last visited Apr. 8, 2021) (Year: 2009).*

(Continued)

*Primary Examiner* — Elaine Gort
*Assistant Examiner* — Nicholas Akogyeram, II

(57) ABSTRACT

A method of collecting test data from use of a disposable test kit, the method comprising the steps of: a code reader scanning a unique test identifier provided on the disposable test kit; an identification module identifying from the scanned unique test identifier a type of test performed by the disposable test kit; the code reader scanning a patient identifier; the identification module identifying from the scanned patient identifier a patient who has used the disposable test kit; a display and selection module automatically displaying on a display screen each of all possible distinct outcomes associated with the identified test as a selectable option; a user selecting one of the displayed all possible distinct outcomes for collection as test data; an association module automatically associating the test data (Continued)

with the patient; and the user activating storage of the test data to a data storer.

13 Claims, 2 Drawing Sheets

(51) Int. Cl.
*G16H 10/40* (2018.01)
*G06F 3/0482* (2013.01)
*G06K 7/14* (2006.01)
*G01N 33/50* (2006.01)

(52) U.S. Cl.
CPC ........... *G06K 7/1417* (2013.01); *G16H 10/40* (2018.01); *B01L 3/5023* (2013.01); *B01L 2300/021* (2013.01); *B01L 2300/024* (2013.01); *B01L 2300/0825* (2013.01); *G01N 33/50* (2013.01); *Y02A 90/10* (2018.01)

(56) References Cited

U.S. PATENT DOCUMENTS

| | | | | |
|---|---|---|---|---|
| 2003/0073124 A1* | 4/2003 | Bowman | ................ | G06Q 50/22 435/6.11 |
| 2006/0180659 A1* | 8/2006 | Loffredo | ................ | G16H 40/20 235/380 |
| 2007/0179356 A1* | 8/2007 | Wessel | ................ | G16H 40/63 600/300 |
| 2007/0292941 A1 | 12/2007 | Handique et al. | | |
| 2009/0048870 A1* | 2/2009 | Godshall | ................ | G06Q 50/24 705/3 |
| 2010/0160757 A1* | 6/2010 | Weinert | ................ | G06F 19/3456 600/365 |
| 2010/0196200 A1 | 8/2010 | Lee | | |
| 2011/0112861 A1* | 5/2011 | Hama | ................ | G06Q 50/22 705/2 |
| 2012/0071342 A1 | 3/2012 | Lochhead et al. | | |
| 2012/0143624 A1* | 6/2012 | Jena | ................ | G06Q 50/22 705/3 |
| 2012/0288851 A1 | 11/2012 | Kasai et al. | | |
| 2014/0100791 A1* | 4/2014 | Darmstadt | ........ | G01N 35/00732 702/19 |
| 2014/0161667 A1* | 6/2014 | Kokic | ................ | G06Q 50/22 422/68.1 |
| 2015/0301031 A1* | 10/2015 | Zin | ................ | G01N 27/02 436/164 |
| 2016/0110523 A1* | 4/2016 | Francois | ................ | G06Q 50/24 705/2 |

FOREIGN PATENT DOCUMENTS

| | | | |
|---|---|---|---|
| TW | 201217783 A1 | 5/2012 | |
| WO | WO-2005111086 A2 * | 11/2005 | ............. G16H 40/63 |
| WO | 2014066704 A1 | 5/2014 | |
| WO | 2017003368 A1 | 1/2017 | |

OTHER PUBLICATIONS

Foreign Communication from a Related Counterpart Application, Chinese Office Action dated Nov. 4, 2019, Chinese Application No. 201580081403.6 filed on Jun. 29, 2015.

Foreign Communication From a Related Counterpart Application, International Search Report and Written Opinion dated Sep. 29, 2015, International Application No. PCT/SG2015/050185 filed Jun. 29, 2015.

Foreign Communication from a Related Counterpart Application, Taiwanese Office Action dated Nov. 29, 2019, Taiwanese Application No. 105119451 filed on Jun. 29, 2015.

* cited by examiner

METHOD AND APPARATUS FOR COLLECTING TEST DATA FROM USE OF A DISPOSABLE TEST KIT

CROSS-REFERENCE TO RELATED APPLICATIONS

The present application is a filing under 35 U.S.C. 371 as the National Stage of International Application No. PCT/SG2015/050185, filed Jun. 29, 2015, entitled "METHOD AND APPARATUS FOR COLLECTING TEST DATA FROM USE OF A DISPOSABLE TEST KIT," which is incorporated herein by reference in its entirety for all purposes.

FIELD OF THE INVENTION

This invention relates to a method and apparatus for collecting test data from use of a disposable test kit.

BACKGROUND OF THE INVENTION

Disposable test kits such as home pregnancy test kits or laboratory test kits using bodily fluids such as urine or blood as an analyte to detect or diagnose disease or other medical conditions are in common use throughout the world. It is necessary to collect test data from using such disposable test kits, in order to monitor a patient's medical condition and/or for other purposes such as statistical data collection. However, mix-ups are known to occur when linking patients with their individual test data collected, and for health care organisations and patients alike, the task of storing and organising vast volumes of test data collected would benefit from being as simple to perform and as streamlined as possible.

SUMMARY OF INVENTION

According to a first aspect, there is provided a method of collecting test data from use of a disposable test kit, the method comprising the steps of: a code reader scanning a unique test identifier provided on the disposable test kit; an identification module identifying from the scanned unique test identifier a type of test performed by the disposable test kit; the code reader scanning a patient identifier; the identification module identifying from the scanned patient identifier a patient who has used the disposable test kit; a display and selection module automatically displaying on a display screen each of all possible distinct outcomes associated with the identified test as a selectable option, a user selecting one of the displayed all possible distinct outcomes for collection as test data; an association module automatically associating the test data with the patient; and the user activating storage of the test data to a data storer.

The selecting one of the displayed all possible distinct outcomes for collection as test data may be such that the one of the displayed all possible distinct outcomes selected by the user corresponds to an actual outcome of the test arising from use of the disposable test kit by the patient.

The method may further comprise the steps of: taking a photograph of the actual outcome of the test on the disposable test kit; automatically associating the photograph with the test data; and storing the photograph to the data storer.

The method may further comprise the step of: an alerting module automatically prompting the patient to perform a predetermined action based on the test data The automatically prompting the patient to perform a predetermined action based on the test data may include the alerting module comparing the test data with previously collected test data and selecting the predetermined action from a database of predetermined actions according to results of the comparing.

The unique test identifier may comprise a quick response code having information about the type of test stored therein.

The data storer may be a database on a server made accessible to a healthcare organisation via a subscription service.

Each of all possible distinct outcomes may be displayed as an image corresponding to what the patient would see on the disposable test kit for each possible distinct outcome arising from use of the disposable test kit.

The method may further comprise automatically displaying on the display screen a distinct test result corresponding with the test data after the user has selected one of the displayed all possible distinct outcomes for collection as test data and before the user activates storage of the test data to the data storer.

According to a second aspect, there is provided an apparatus for collecting test data from use of a disposable test kit, the apparatus comprising: a code reader configured to scan a unique test identifier provided on the disposable test kit and further configured to scan e patient identifier; an identification module configured to identify from the scanned unique test identifier a type of test performed by the disposable test kit and further configured to identify from the scanned patient identifier a patient who has used the disposable test kit; a display screen: a display and selection module configured to automatically display on the display screen each of all possible distinct outcomes associated with the identified test as a selectable option for selection by a user such that only a selected one of the displayed all possible distinct outcomes is collected as test data; an association module configured to automatically associate the test data with the patent; and a data storer configured to automatically store the test data upon activation by the user.

The apparatus may further comprise a camera configured to take a photograph of an actual outcome of the test on the disposable test kit, wherein the association module is further configured to automatically associate the photograph with the test data, and wherein the data stoner is further configured to automatically store the photograph in the data storer.

The apparatus may further comprise an alerting module configured to automatically prompt the identified patient to perform a predetermined action based on the test data.

The alerting module may be further configured to compare the test data with previously collected test data and to select the predetermined action from a database of predetermined actions according to different results of the comparing.

The unique test identifier may further comprise a quick response code having information about the type of test stored therein.

The data storer may be a database on a server made accessible to a healthcare organisation via a subscription service.

Each of all possible distinct outcomes may be displayed as an image corresponding to what the patient would see on the disposable test kit for each possible distinct outcome arising from use of the disposable test kit.

The display and selection module may be further configured to automatically display on the display screen a distinct test result corresponding with the test data.

According to a third aspect, there is provided a computer program stored on tangible computer readable medium, said program comprising computer readable code which, when executed on a processor, causes the processor to perform the steps of the method of the first aspect that are not performed by the user.

According to a fourth aspect, there is provided a computer program product comprising a tangible computer readable medium and a computer program according to the third aspect, wherein the computer program is stored on the tangible computer readable medium.

BRIEF DESCRIPTION OF FIGURES

In order that the invention may be fully understood and readily put into practical effect there shall now be described by way of non-limitative example only exemplary embodiments of the present invention, the description being with reference to the accompanying illustrative drawings.

DETAILED DESCRIPTION

Figure 2:
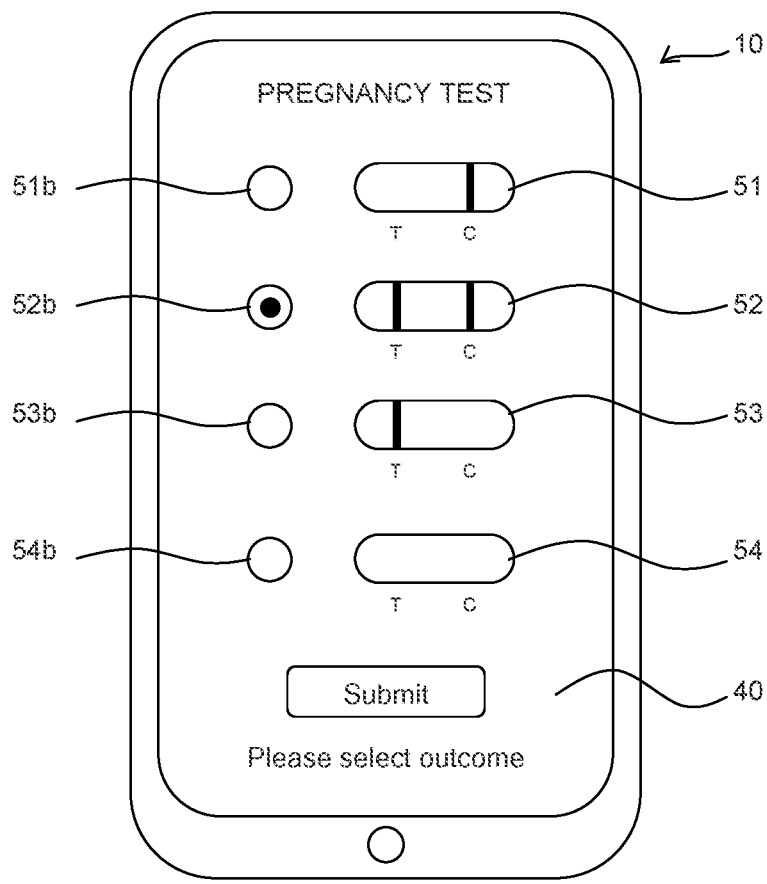
FIG. 2 is a schematic illustration of an exemplary display of all possible test outcomes during use of the apparatus and method.
Figure 3:
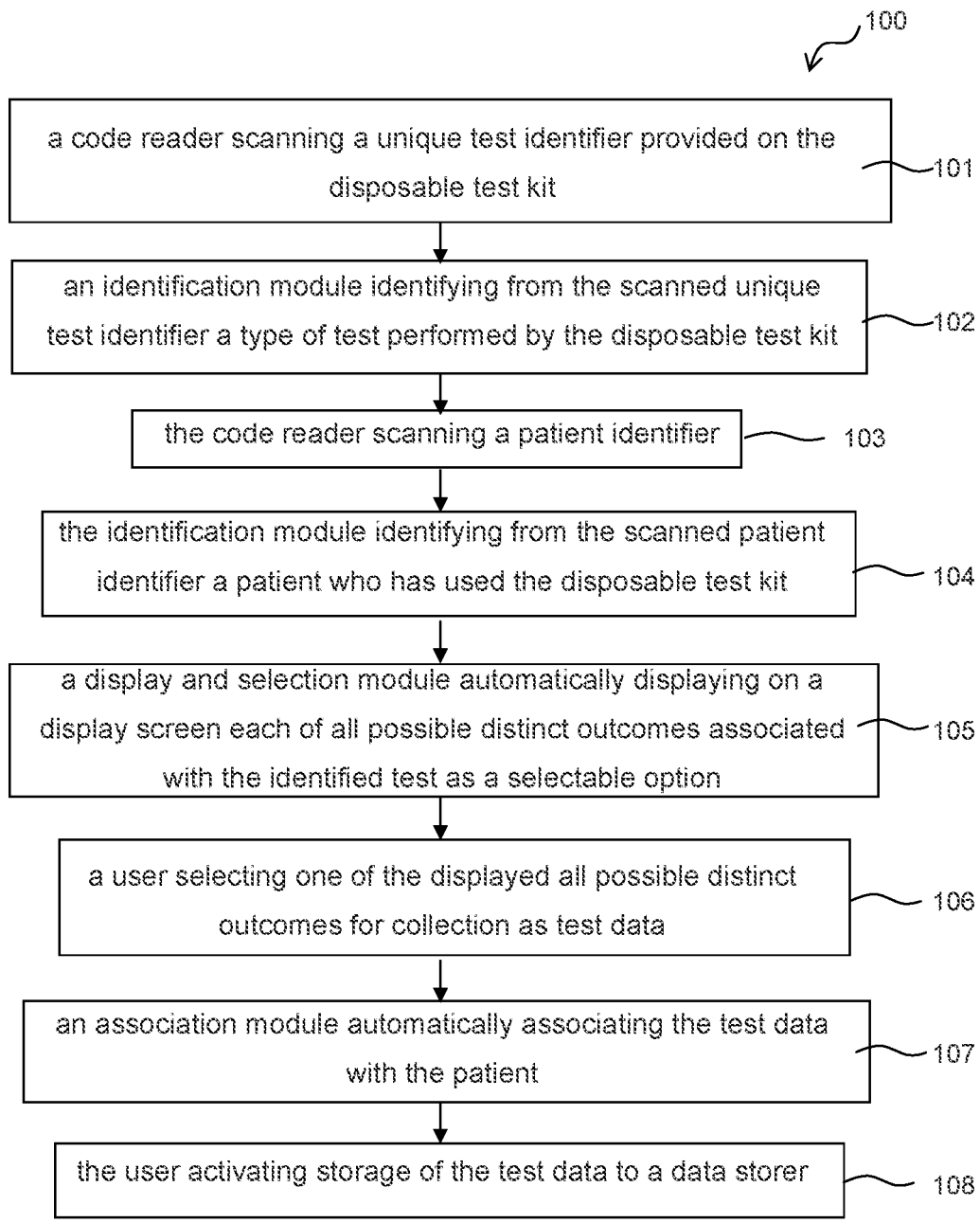
FIG. 3 is a flow chart of an exemplary method of collecting test data from a disposable test kit.

Exemplary embodiments of a method 100 and apparatus 10 for collecting test data from a disposable test kit will be described below with reference to FIGS. 1 to 3, in which the same reference numerals are used to denote the same or similar parts.

Figure 1:
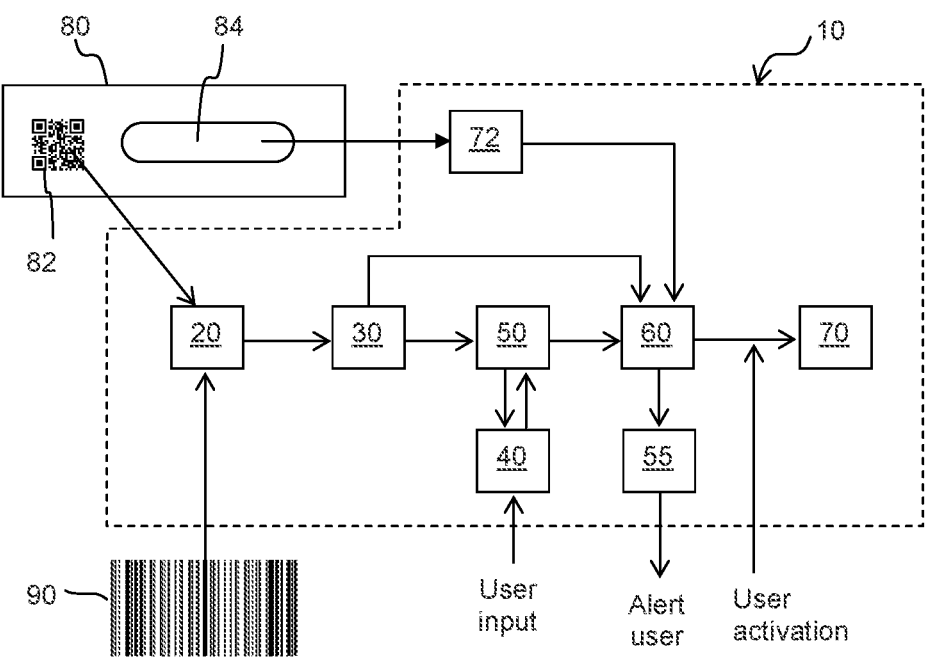
FIG. 1 is a an exemplary architectural diagram of an apparatus for collecting test data from a disposable test kit.

As shown in FIG. 1, the apparatus 10 for collecting test data from use of a disposable test kit 60 comprises a code reader 20 configured to scan a unique test identifier 82 provided on the disposable test kit 80 and to scan a patient identifier 90 In a preferred embodiment, the unique test identifier 82 is in the form of a quick response code while the patient identifier 90 is a bar code that may be provided on an identification card or a clinical record of the patient.

The apparatus 10 also comprises an identification module 30 configured to identify from the scanned unique test identifier 82 a type of test performed by the disposable test kit 80 and to identify from the scanned patient identifier 90 a patient who has used the disposable test kit 80, from whom the fluid analytes obtained to run the test performed by the disposable test kit 80. The test performed by the disposable test kit 80 is an immunoassay carried out by analysing a fluid analyte using a dipstick or lateral flow test stop provided in the disposable test kit 80.

Currently, different types of immunoassays are available to test for different medical conditions or to detect or diagnose disease. Examples of different types of tests that may be performed using a disposable test kit include pregnancy test, human immunodeficiency virus (HIV) test, urine test, Malaria test, Dengue test, Leptospira test, Typhoid Fever test and so on. Appreciably, each test has its own specific possible distinct outcomes. For example, in a pregnancy test, there may be four possible distinct outcomes: a negative outcome indicated by only one visible line shown in a result window 84 of the disposable test kit 80 at a 'control' location, a positive outcome indicated by two visible lines shown in the result window 84, and two invalid outcomes: a first invalid outcome indicated by no visible line at the 'control' location and a visible line at the 'test' location, and a second invalid outcome indicated by no visible line at the 'control' location and no visible line at the 'test' location. The 'test' location may be marked by "T" to represent Test, and the 'control' location may be marked by "C" to represent Control in the result window 84.

The apparatus 10 further comprises a display screen 40 and a display and selection module 50 configured to automatically display on the display screen 40 each of all possible distinct outcomes associated with the identified test as a selectable option for selection by a user. This may be achieved by displaying each of the possible distinct outcomes 51, 52, 53, 54 on the screen together with its own option button 51*b*, 52*b*, 53*b*, 54*b* as shown in FIG. 2. Each option button 51*b*, 52*b*, 53*b*, 54*b* may be selected by touching that option button if the display screen is a touch screen, or using a mouse to click on the option button if the display screen is connected to a computing device having a mouse input. Alternatively, each of the possible distinct outcomes may be displayed as a selectable item itself without any option buttons required so that selection is made by touching or mouse-clicking on one of the possible distinct outcomes directly.

In a preferred embodiment, each of the possible distinct outcomes is displayed as an image of a result window that corresponds with what the patient of the disposable test kit 80 would see in the result window for that particular outcome as arising from use of the disposable test kit 80. For example, if the disposable test kit was a pregnancy test having four possible distinct outcomes, all four possible distinct outcomes would be displayed as a first image of result window 84 showing one visible line at the 'control' location for a negative outcome 51, a second image of a result window showing two visible lines for a positive outcome 52, a third image of a result window showing one visible line at the 'test' location but no visible line at the 'control' location 53 for a first invalid outcome, and a fourth image of a result window showing no visible lines for a second invalid outcome 54. In this way, the user is presented with a multiple choice assessment in which the user can select an option that visually matches an actual outcome of the test that is visible on the disposable test kit after use of the disposable test kit by the patient.

The apparatus 10 is configured such that only the selected one of the displayed possible distinct outcomes is collected as test data.

In a preferred embodiment, the display and selection module 50 is further configured to automatically display on the display screen 40 a distinct test result corresponding with the test data after selection of one of the possible distinct outcomes by the user. In this way, the user does not need to mentally interpret the outcome of the test that is visible on the disposable test kit 80, but only needs to select a displayed image on the display screen that matches what is seen on the disposable test kit, and a distinct test result is automatically displayed. Continuing with the example of the disposable test kit 80 being a pregnancy test Kit, upon the user selecting the second image 52 as shown in FIG. 2, a result such as "Pregnancy Positive" or the like will be displayed on the display screen. To facilitate this feature, the distinct test results that are known to correspond with the possible distinct outcomes of the test are stored in a library accessible to the display and selection module 50.

The apparatus 10 further comprises an association module 60 configured to automatically associate the test data with the identified patent. In this way, test data can be stored for each specific patient and mix-ups between patients and test outcomes can be eliminated.

The apparatus 10 also comprises a data storer 70 configured to automatically store the test data in the data storer 70 upon activation by the user. The data storer 70 may be one or more of an internal memory of a computing device such as a smart phone or hard disk of a computer, an external storage device such as an SD card or flash memory device, a cloud computing storage, a database on a server and so on. Additionally, test data in the data storer 70 may be configured to be made accessible to a healthcare organisation via a subscription service. Storage of the tested data to the data storer 70 is configured to be activated by the user, for example, by touching or clicking on a "save" icon displayed on the display screen after selection of one of the possible distinct outcomes.

Optionally, the apparatus 10 may further comprise a camera 72 configured to take a photograph of an actual outcome of the test on the disposable test kit 80. In such an embodiment, the association module 60 is further configured to automatically associate the photograph with the test data, and the data storer 70 is further configured to automatically store the photograph. The photograph is intended to serve as evidence and as a back-up to check that the test data corresponds with the actual outcome of the test on the disposable test kit 80.

The apparatus 10 may also further comprise an alerting module 55 configured to automatically prompt the patient to perform a predetermined action based on the test data. For example, in the case where the type of test is a blood sugar level test, if the test data indicates that the blood sugar level is beyond a predetermined level, the alerting module may prompt the patient to see their doctor. Prompting the patient may be by means of sending an sms or an email to the patient, or displaying on the display screen an appropriate message. Additionally, the alerting module 55 may be further configured to compare the test data with previously collected test data and to select the predetermined action from a database of predetermined actions according to different results of the comparing. This is envisaged for test in which different magnitudes of change between the test data and previously collected test data require different actions to be taken. For example, where the apparatus 10 is configured as an HBA1c (refers to glycated haemoglobin (A1c), which identifies average plasma glucose concentration) glucose monitoring device, test data collected will be captured each time a user saves the latest test results. If the latest collected test data exceeds a predetermined difference when compared with the previously collected data, the patient will be prompted to take a predetermined appropriate action according to the magnitude of the difference.

One embodiment of the apparatus 10 is in the form of a smart phone (as already shown in FIG. 2) in which the code reader 20 is provided as an application making use of the camera provided in the smart phone, and the display screen 40 is the display screen of the smart phone. The identification module 30, the display and selection module 50, the association module 60 and the alerting module 55 (optional) are provided in an application configured to work with the operating system of the smart phone. The data storer 70 may include the internal memory of the smart phone as well as a database on a server that is accessed via cloud computing. The smart phone embodiment is particularly suited for point-of-care use in which the user and the patient who uses the disposable test kit are expected to be the same person, or in which the user is a caregiver of the patient.

An alternative embodiment of the apparatus 10 is in the form of a computer (not shown) in which the code reader 20 is provided as a handheld or stationary laser barcode scanner and the display screen 40 is a monitor of the computer. The identification module 30, the display and selection module 50, the association module 80 and the alerting module 55 (optional) are provided as a software application configured to work with the operating system of the computer. The data scorer 70 may include the internal hard disk of the computer as well as a database on a network server to which the computer is connected. The computer embodiment is particularly suited for organisational use in which the user may be a staff member of the organisation facilitating the collection of test data from multiple patients each using a unique disposable test kit.

The method 100 of collecting test data from use of the disposable test kit will now be described with reference to FIG. 3. In the method 100, the code reader 20 is used to scan a unique test identifier 82 provided on the disposable test kit 80 (101) and from the scan, the identification module 30 identifies a type of test performed by the disposable test kit (102). The code reader 20 is also used to scan a patient identifier 90 (103) from which the identification module 30 identifies the patient who used the disposable test kit (104). The display and selection module 50 then automatically displays each of all possible distinct outcomes associated with the identified test on the display screen 40 as a selectable option (105). The user selects one of the displayed outcomes for collection as test data (106). The selecting step (106) should be such that the outcome selected by the user corresponds to an actual outcome of the test arising from use of the disposable test kit by the patient. The association module 60 then automatically associates the test data with the patient (107) and the user finally activates storage of the test data to the data storer 70 (108).

The method (100) may optionally further comprise taking a photograph of the actual outcome of the test on the disposable test kit, automatically associating the photograph with the test data and storing the photograph to the data storer. Storing of the photograph may be user activated or automatically performed.

Depending on the test data, the method may further automatically prompt the patient to perform a predetermined action based on the test data. This may comprise sending an electronic message to the patient The automatically prompting may include comparing the test data with previously collected test data and selecting the predetermined action from a database of predetermined actions according to results of the comparing.

The apparatus 10 and method 100 thus allow test data to be collected without requiring the user to mentally interpret what is seen on the disposable test kit 80. The user only needs to input into the apparatus 10 what the user sees on the disposable test kit 80 without having to interpret what the test outcome means. Interpretation is performed by the apparatus 10 according to the input test outcome that has been predetermined to correlate with a specific test result. This reduces one possible source of human error. At the same time, the apparatus 10 and method 100 do not rely on using the apparatus 10 to automatically read the test outcome shown by the disposable test kit 80, since it is the user who selects one of the possible distinct outcomes displayed by the apparatus 10 according to what the user sees on the disposable test kit 80. The method 100 and apparatus 10 thus combine the strengths of human and machine capabilities while reducing possibilities of human and machine error.

Whilst there has been described in the foregoing description exemplary embodiments of the present invention, it will be understood by those skilled in the technology concerned that many variations in details of design, construction and/or operation may be made without departing from the present invention.

The invention claimed is:

1. A method of collecting test data from use of a disposable test kit, the method comprising the steps of:
   a) a code reader scanning a unique test identifier provided on the disposable test kit;
   b) an identification module stored in a non-transitory memory and executable by a processor identifying from the scanned unique test identifier a type of test performed by the disposable test kit;
   c) the code reader scanning a patient identifier;
   d) the identification module identifying from the scanned patient identifier a patient who has used the disposable test kit;
   e) a display and selection module automatically displaying on a display screen a graphical user interface (GUI) comprising each of all possible distinct outcomes associated with the identified type of test as a selectable option in response to the identification module identifying the type of test from the scanned unique test identifier on the disposable test kit, wherein each of all possible distinct outcomes is displayed in the GUI as an image corresponding to what the patient would see on the disposable test kit for each possible distinct outcome arising from use of the disposable test kit;
   f) receiving via the GUI a user input indicating selection of one of the displayed all possible distinct outcomes for collection as test data;
   g) an association module stored in a non-transitory memory and executable by a processor automatically associating the test data with the patient;
   h) the user activating storage of the test data to a data storer; and
   i) an alerting module stored in a non-transitory memory and executable by a processor comparing the test data with previously collected test data, selecting a predetermined action from a database of predetermined actions according to results of the comparing, and automatically electronically transmitting a message to the patient to prompt the patient to perform the predetermined action based on the test data.

2. The method of claim 1, wherein the selecting in step f) is such that the one of the displayed all possible distinct outcomes selected by the user corresponds to an actual outcome of the test arising from use of the disposable test kit by the patient.

3. The method of claim 2, further comprising the steps of:
   j) taking a photograph of the actual outcome of the test on the disposable test kit;
   k) automatically associating the photograph with the test data; and
   l) storing the photograph to the data storer.

4. The method of claim 1, wherein the unique test identifier comprises a quick response code having information about the type of test stored therein.

5. The method of claim 1, wherein the data storer is a database on a server made accessible to a healthcare organisation via a subscription service.

6. The method of claim 1, further comprising: after step f) and before step h), automatically displaying on the display screen a distinct test result corresponding with the test data.

7. An apparatus for collecting test data from use of a disposable test kit, the apparatus comprising:
   a code reader configured to scan a unique test identifier provided on the disposable test kit and further configured to scan a patient identifier;
   an identification module stored in a non-transitory memory that, when executed by a processor, identifies from the scanned unique test identifier a type of test performed by the disposable test kit and identifies from the scanned patient identifier a patient who has used the disposable test kit;
   a display screen;
   a display and selection module configured to automatically display on the display screen a graphical user interface (GUI) comprising each of all possible distinct outcomes associated with the identified type of test as a selectable option for selection by a user via the GUI in response to the identification module identifying the type of test from the scanned unique test identifier on the disposable test kit such that only a selected one of the displayed all possible distinct outcomes is collected as test data, wherein each of all possible distinct outcomes is displayed in the GUI as an image corresponding to what the patient would see on the disposable test kit for each possible distinct outcome arising from use of the disposable test kit;
   an association module stored in a non-transitory memory that, when executed by a processor, automatically associates the test data with the patient;
   a data storer configured to automatically store the test data upon activation by the user; and
   an alerting module stored in a non-transitory memory that, when executable by a processor, compares the test data with previously collected test data, selects a predetermined action from a database of predetermined actions according to results of the comparing, and automatically electronically transmitting a message to the patient to prompt the patient to perform the predetermined action based on the test data.

8. The apparatus of claim 7, further comprising a camera configured to take a photograph of an actual outcome of the test on the disposable test kit, wherein the association module is further configured to automatically associate the photograph with the test data, and wherein the data storer is further configured to automatically store the photograph in the data storer.

9. The apparatus of claim 7, wherein the unique test identifier comprises a quick response code having information about the type of test stored therein.

10. The apparatus of claim 7, wherein the data storer is a database on a server made accessible to a healthcare organisation via a subscription service.

11. The apparatus of claim 7, wherein the display and selection module is further configured to automatically display on the display screen a distinct test result corresponding with the test data.

12. A computer program stored on a non-transitory, tangible computer readable medium, said program comprising computer readable code which, when executed on a processor, causes the processor to perform the steps of claim 1 that are not performed by the user.

13. A computer program product comprising a non-transitory, tangible computer readable medium and a computer program according to claim 12, wherein the computer program is stored on the non-transitory, tangible computer readable medium.

* * * * *